(12) United States Patent
Redshaw

(10) Patent No.: US 7,247,296 B2
(45) Date of Patent: Jul. 24, 2007

(54) RADIATION THERAPY BY ACCUMULATION OF THERAPEUTIC RADIONUCLIDES IN TUMOR-TARGETING BACTERIA

(75) Inventor: Russell Redshaw, Ottawa (CA)

(73) Assignee: MDS (Canada) Inc., Ontario (CA)

( * ) Notice: Subject to any disclaimer, the term of this patent is extended or adjusted under 35 U.S.C. 154(b) by 0 days.

(21) Appl. No.: 11/330,017

(22) Filed: Jan. 11, 2006

(65) Prior Publication Data

US 2006/0104955 A1    May 18, 2006

Related U.S. Application Data

(63) Continuation of application No. 10/301,517, filed on Nov. 20, 2002, now Pat. No. 7,015,027.

(60) Provisional application No. 60/332,669, filed on Nov. 20, 2001.

(51) Int. Cl.
*A01N 63/00* (2006.01)
*A01N 65/00* (2006.01)

(52) U.S. Cl. ............... 424/93.1; 424/93.2; 424/93.4

(58) Field of Classification Search ............... 424/93.1, 424/93.2, 93.4
See application file for complete search history.

(56) References Cited

U.S. PATENT DOCUMENTS

| | | | |
|---|---|---|---|
| 5,816,259 A | 10/1998 | Rose | |
| 6,015,376 A | 1/2000 | Ain et al. | |
| 6,080,849 A | 6/2000 | Bermudes et al. | |
| 6,190,657 B1 | 2/2001 | Pawelek et al. | |
| 6,391,579 B1 | 5/2002 | Carrasco et al. | |
| 6,586,411 B1 | 7/2003 | Russell et al. | |
| 6,685,935 B1 | 2/2004 | Pawelek et al. | |
| 6,803,199 B2 | 10/2004 | Carrasco et al. | |
| 7,015,027 B1 | 3/2006 | Redshaw | |

FOREIGN PATENT DOCUMENTS

| WO | WO-96/40238 | 12/1996 |
|---|---|---|
| WO | WO-97/18837 | 5/1997 |
| WO | WO-01/13106 A1 | 2/2001 |

OTHER PUBLICATIONS

Adler, J. , "A Method For Measuring Chemotaxis and Use of the Method to Determine Optimum Conditions for Chemotaxis by *Escherichia coli*", *Journal of General Microbiology 74*, (1972),77-91.

Barrows, Louis R., "Evidence for the Cloningof *Deinococcus radiodurans* DNA Fragments that Render *Escherichia coli* Radiation Resistant", *Radiation Research 120*, (1989),pp. 537-544.

Battista, Joihn R., et al., "Radiation Resistance: The Fragments that Remain", *Current Biology*, 10(5), (Mar. 9, 2000),R204-R205.

Battista, John R., et al., "Why is *Deinococcus radiodurans* So Resistant to Ionizing Radiation", *Trends in Microbiology*, 7(9), (Sep. 1999),362-365.

Bauche, Cecile , et al., "Repair of Oxidized Bases in the Extremely Radiation-Resistant Bacterium *Deinococcus radiodurans*", *Journal of Bactriology*, 181(1), (Jan. 1999),262-269.

Benvenga, S , et al., "Homologies of the Thyroid Sodium-Iodide Symporter With Bacterial and Viral Proteins", *Journal Endocrinol Invest*, 22(7), (Jul.-Aug. 1999),535-540.

Bermudes, David , et al., "Tumor-Targeted *Salmonella*", *Cancer Gene Therapy*, (2000),pp. 57-63.

Boland, Anne , et al., "Adenovirus-Mediated Transfer of the Thyroid Sodium/Iodide Symporter Gene Into Tumors for a Targeted Radiotherapy", *Cancer Research 60.*, (Jul. 2000),pp. 3484-3492.

Braverman, Lewis E., et al., "The Thyroid", *Werner & Ingbar, 7th Ed*, (1996),pp. 922-945.

Brown, J. M., "Hypoxic Cell Radiosensitizers: Where Nex?", *Journal of Radiation Oncology—vol. 16*, (1988),pp. 987-993.

Carlin, Sean , et al., "Experimental Targeted Radioiodide Therapy Following Transfection of the Sodium Iodide Symporter Gene: Effect on Clonogenicity in Both Two-And-Three-Dimensional Models", *Cancer Gene Therapy*, 7(12), (2000),1529-1536.

Clairmont, C. , et al., "Biodistribution and Genetic Stability of the Novel Antitumor Agent VNP20009, A Genetically Modified Strain of *Salmonella typhimurium*", *The Journal of Infectious Diseases*, (2000),pp. 1996-2002.

Dadachova, E. , et al., "Rhenium-188 As An Alternative to Iodine-131 for Treatment of Breast Tumors Expressing the Sodium/Iodide Symporter (NIS)", *Nuclear Medicine and Biology 29.*, (2002),pp. 13-18.

Dai, GE , et al., "Cloning and Characterization of The Thyroid Iodide Transporter", *Nature*, vol. 379., (1996),pp. 458-460.

Dalrymple, G. V., et al., "*Deinococcus radiodurans* DNA Increases the Radiation Resistance of *Escherichia coli*", *Radiation Research 120.*, (1989),pp. 532-536.

Daly, Michael J., "Engineering Radiation-Resistant Bacteria For Environmental Biotechnology", *Current Opinion in Biotechnology*, (2000),pp. 280-285.

Denardo, Diane A., et al., "Prediciton of Radiation Doses from Therapy Using Tracer Studies with Iodine-131-Labeled Antiobodies", *The Journal of Nuclear Medicine*, vol. 37, (1996),pp. 1970-1975.

Galen, James E., et al., "Optimization of Plasmid Maintenance in the Attenuated Live Vector Vaccine Strain *Salmonella typhi* CVD 908-htrA", *Infection and Immunity.*, (Dec. 1999),6424-6433.

Haberkorn, U. , "Gene Therapy With Sodium/Iodide Symporter in Hepatocarcinoma", *Exp Clin Endocrinol Diabetes 109.*, (2001),pp. 60-62.

(Continued)

*Primary Examiner*—Mark Navarro
(74) *Attorney, Agent, or Firm*—Schwegman, Lundberg, Woessner and Kluth P.A.

(57) ABSTRACT

The invention can be summarized as follows. According to the present invention there is provided an attenuated, tumour-targeting bacterium comprising a heterologous nucleotide sequence encoding a protein permitting the accumulation of a radionuclide within the bacterium. The heterologous nucleotide sequence may encode a sodium iodide symporter protein. The invention also relates to the use of such bacteria and methods of treating diseases using the bacteria of the present invention.

6 Claims, No Drawings

OTHER PUBLICATIONS

Hlavalty, J., et al., "Construction and Testing of Gene Therapy Retroviral Vector Expressing Bacterial Cytosine Deaminase Gene", *Neoplasma 46.*, (1999),pp. 267-276.

Hoiseth, Susan K., et al., "Aromatic-Dependent *Salmonella typhimurium* Are Non-Virulent and Effective as Live Vaccines", *Nature* vol. 291, (May 1981),pp. 238-239.

Huang, Min, et al., "Ectopic Expression of the Thyroperoxidase Gene Augments Radioiodide Uptake and Retention Mediated By the Sodium Iodide Symporter in Non-Small Cell Lung Cancer", *Cancer Gene Therapy*, vol. 8., (2001),pp. 612-618.

Jakopitsch, Christa, et al., "Catalase-Peroxidase from Synechocystis Is Capable of Chlorination and Bromination Reactions", *Biochemical & Biophysical Research Comm 287*, (2001),pp. 682-687.

Jones, Bradley D., et al., "Invasion by *Salmonella typhimurium* Is Affected by the Direction of Flagellar Rotation", *Am Society for Microbiology*, (Jun. 1992),pp. 2475-2480.

Lambin, P., et al., "The Potential Therapeutic Gain of Radiation-Associated Gene Therapy With the Suicide Gene Cytosine Deaminase", *Int. J. Radiat. Biol.*, vol. 76, No. 3., (2000),pp. 285-293.

Lee, Catherine A., et al., "Identification of a *Salmonella typhimurium* Invasion Locus by Selection for Hyperinvasive Mutants", *Proc. Nat'l Acad. Sci, USA*, vol. 89., (Mar. 1992),pp. 1847-1851.

Levy, Orlie, et al., "Characterization of the Thyroid Na+/I-Symporter With An Anti-COOH Terminus Antibody", *Proc. Nat'l Acad. Sci. USA*, vol. 94, pp. 5568-5573.

Macey, Daniel J., et al., "A Radioimmunoimaging and MIRD Dosimetry Treatment Planning Program for Radioimmunotherapy", *Nuclear Medicine & Biology*, vol. 23., (1996),pp. 525-532.

Mandell, Robert B., et al., "Radioisotope Concentrator Gene Therapy Using the Sodium/Iodide Symportr Gene", *Cancer Research 59,*, (Feb. 1999),pp. 661-668.

O'Callaghan, David, et al., "High Efficiency Transformation of *Salmonella typhimurium* and *Salmonnela typhi* by Electroporation", *Mol Gen Genet 223*, (1990),pp. 156-158.

Pawleek, John M., et al., "Tumor-Targeted *Salmonella* As A Novel Anticancer Vector", *Cancer Research.*, (Oct. 1977),pp. 4537-4544.

Roy, Astrid M., et al., "Mutations in firA, Encoding the Second Acyltransferase in Lipopolysaccharide Biosynthesis, Affect Multiple Steps in Lipopolysaccharide Biosynthesis", *Journal of Bacteriology*, (Mar. 1994),pp. 1639-1646.

Somerville, John E., et al., "A Novel *Escherichia coli* Lipid A Mutant That Produces an Antiinflammatory Lipopolysaccharide", *The American Society for Clinical Investigation, Inc.*, (Jan. 1996),pp. 359-365.

Spitzweg, Christine, et al., "Analysis of Human Sodium Iodide Symporter Gene Expression in Extrathyroidal Tissues and Cloning of its Complementary Deoxyribonucleic Acids from Salivary Gland, Mammary Gland, and Gastric Mucosa", *Journal of Clinical Endocrinology and Metabolism*, (1998),pp. 1746-1751.

Spitzweg, Christine, et al., "Approaches to Gene Therapy with Sodium/Iodide Symporter", *Exp Clinical Endocrinoll Diabetes 109*, pp. 56-59.

Spitzweg, Christine, et al., "Prostate-Specific Antigen (PSA) Promoter-Driven Androgen-Indicible Expression of Sodium Iodide Symporter in Prostate Cancer Cell Lines", *Cancer Research 59*, (May 1999),pp. 2136-2141.

Spitzweg, Christine, et al., "The Sodium Iodide Symportr and Its Potential Role in Cancer Therapy", *The Journal of Clinical Endocrinology and Metabolism*, (2001),pp. 3327-3335.

Spitzweg, Christine, et al., "Treatment of Prostate Cancer by Radioiodine Therapy after Tissue-Specific Expression of the Sodium Iodide Symporter", *Cancer Research 60,*, (Nov. 2000),pp. 6526-6530.

"Cellular, Molecular, and Tumor Biology 7", *Proceeding of the American Association for Cancer Research*, vol. 45, (Mar. 2004), 50-51.

"Sodium Iodide, 131 Solution Rx Only", *Sodium Iodide, 131 Solution 450*, 2 Pages.

"Summary of Current Radiation Dose Estimates to Humans From 123, 124, 125, 126, 130, 131, and 132 as sodium iodide", *mird/Dose Estimate Report No. 5, Journal of Nuclear Medicine*, vol. 16, No. 9, (Sep. 1975), 857-860.

Saha, Ph.D., Gopal B., "Therapeutic Uses of Radiopharmaceuticals in Nuclear Medicine", *Fundamentals of Nuclear Pharmacy, Fourth Edition, Chapter 14*, 320-323.

Shen, Dhy, et al., "Effects of dose, intervention time, and radionuclide on sodium iodide symporter (NIS)-targeted radionuclide therapy", *Gene Therapy*, vol. 11, (2004), 161-169.

RADIATION THERAPY BY ACCUMULATION OF THERAPEUTIC RADIONUCLIDES IN TUMOR-TARGETING BACTERIA

RELATED APPLICATIONS

This application is a continuation under 37 C.F.R. 1.53(b) of U.S. application Ser. No. 10/301,517 filed Nov. 20, 2002 now U.S. Pat. No. 7,015,027, which claimed the benefit of U.S. provisional application No. 60/332,669 filed on Nov. 20, 2001, which applications are incorporated herein by reference.

FIELD OF THE INVENTION

The invention relates to tumor-targeting bacteria. More specifically the present invention relates to tumor-targeting bacteria that accumulate radionuclides and the use of these bacteria to deliver a dose of radioactivity to a tumor within a subject.

BACKGROUND OF THE INVENTION

Numerous therapies exist for the treatment of tumors including gene therapy, radiation therapy and chemotherapy. Of these therapies, radiation therapy is recognized as one of the most important methods of treating tumors. The objective of radiation therapy is to optimize the radiation delivered to the tumor while sparing normal tissue.

For approximately half a century, thyroid cancer has been effectively treated with $^{131}$I. Sodium iodide is preferentially taken up by thyroid cells where it is oxidized and incorporated onto tyrosine and ultimately incorporated into triiodothyronine (T3) and thyroxine (T4). Success in the procedure to effectively treat metastatic thyroid cancer is evident by the low mortality of patients treated with $^{131}$I (Spitzweg et al., 1999; Mazzaferri, (1996)).

Uptake of iodine by the thyroid is performed by a membrane-bound glycoprotein termed the sodium/iodide symporter (NIS; Dia et al., 1996). NIS has been expressed in different cell types. For example, WO 07/28175 discloses nucleic acids encoding human NIS, methods of producing NIS, probes for the purpose of diagnosing thyroid disorders, and methods of treating disease by using viral vectors to transfect cells with NIS and later ablate with radioiodine. Mandell et al., (1999) disclose retrovirus transfection and expression of the sodium iodide symporter within a range of tumor cell lines. Boland et al., (2000) disclose a method of providing conformal radiation therapy to non-thyroid cancers by gene therapy whereby the NIS gene is transferred into tumor cells by a recombinant adenovirus. The genetically modified tumor cells exhibit selective and significant uptake of $^{131}$I. Spitzweg et al., (1999; 2000 and 2001) describe NIS applications for gene therapy and in particular the potential application of NIS to treat prostate cancer. Habercorn, (2001) describes NIS gene therapy for the treatment of liver cancer. The reference teaches that transfection of non-thyroid cells with NIS results in cells capable of concentrating iodide approximately 20 to 40 fold above the plasma iodide concentration. Further, the reference teaches that a sufficient amount of radioiodine can be concentrated in transfected cells in vivo to bring about localized radiation therapy with a single dose of $^{131}$I.

The references discussed above disclose transforming tumor cells with a NIS gene by chemical transformation methods, electrical transformation methods or viral transformation methods to enable selective and significant uptake of $^{131}$I into tumor masses. A drawback of these references is that chemical, electrical and viral transformation methods are difficult to perform in-vivo. Further, in-vivo transformation of cells by viral vectors is difficult to control and thus other normal or healthy cells may be erroneously infected and transformed with genes enabling accumulation of radionuclides. Another drawback of these methods is that they are confined to target local or regional disease, that is the transformation vector must be administered in close proximity to the cells or tissue to be infected rather than administering the transformation vector to a subject at a remote location and having the vector identify and infect the tumor cells.

There is a need in the art for novel or alternative therapies for the treatment of tumors in a subject. Further, there is a need in the art for alternative radiotherapies to viral based gene therapy.

It is an object of the present invention to overcome disadvantages of the prior art.

The above object is met by a combination of the features of the main claims. The sub-claims disclose further advantageous embodiments of the invention.

SUMMARY OF THE INVENTION

The invention relates to tumor-targeting bacteria. More specifically the present invention relates to tumor-targeting bacteria that accumulate radionuclides and the use of these bacteria to deliver a dose of radioactivity to a tumor within a subject.

According to an aspect of an embodiment of the present invention there is provided an attenuated, tumour-targeting bacterium comprising a heterologous nucleotide sequence encoding a protein that promotes accumulation of a radionuclide within the bacterium. Preferably, the heterologous nucleotide sequence comprises the sodium iodide symporter (NIS) gene, more preferably a mammalian NIS gene, still more preferably the human NIS gene. However, the NIS gene may comprise a bacterial NIS gene homologue provided that the gene permits uptake of suitable amounts of radionuclide. The bacterial NIS gene may be selected from the group consisting of *Vibrio paprahaemolyticus, Bacillus subtilis*, and *Xanthobacter* sp.

The present invention further provides attenuated, tumor targeting bacteria as defined above that comprise the radionuclide. The radionuclide may be radio-iodine, for example, but not limited to I-131, I-125, I-123, or a combination thereof.

Also according to the present invention, there is provided an attenuated, tumour-targeting bacteria selected from the group consisting of YS8211 ATCC Accession No. 202026, YS1629 ATCC Accession No. 202025, and YS1170 ATCC accession number 202024, *Salmonella typhimurium* strain 70 (ATCC Accession No. 55686), *Salmonella typhimurium* strain 71 (ATCC Accession No. 55685), *Salmonella typhimurium* strain 72 (ATCC Accession No. 55680), *Salmonella typhimurium* strain $72^{5-3-2}$ (ATCC Accession No. 97179), *Salmonella typhimurium* strain $14028^{pop-1}$ (ATCC Accession No. 55684), *Salmonella typhimurium* strain $14028^{pop-2}$ (ATCC Accession No. 55683), *Salmonella typhimurium* strain $72^{pop-1}$ (ATCC Accession No. 55681), *Salmonella typhimurium* strain $72^{pop-2}$ (ATCC Accession No. 55682), *Salmonella typhimurium* strain YS721 (ATCC Accession No. 55788), *Salmonella typhimurium* strain YS7211 (ATCC Accession No. 55787), *Salmonella typhimurium* strain YS7212 (ATCC Accession No. 55789) and *Salmonella typhimurium* strain YS7213 (ATCC Accession No. 55786); and further comprising a heterologous nucleotide sequence encoding a protein that promotes the accumulation of a radionuclide within the bacteria, when the bacteria is in the presence of the radionuclide. Preferably, the heterologous nucleotide sequence comprises the sodium iodide symporter (NIS) gene.

Further, the present invention contemplates bacteria as defined above further comprising an additional nucleotide sequence encoding a protein of interest. The protein of interest may be selected from the group consisting of proteins interfering with cell cycle repair, tumor cell synchronization, hypoxia, proteins producing nitrous oxide, proteins involved in cellular apoptosis, proteins involved in radiation resistance or any combination thereof.

Also, contemplated by the present invention are bacteria as defined above selected from the group consisting of *Pseudomonas radiora, Deinocuccus* species, *Salmonella* species, including *S. typhimurium, S. choleraesuis, S. enteritidis*, and *S. typhimurium*.

Further, according to the present invention there is provided the use of an attenuated, tumour-targeting bacterium comprising a heterologous nucleotide sequence encoding a protein that promotes accumulation of a radionuclide within the bacterium, for the treatment of a tumor in a subject. Preferably, the nucleotide sequence comprises the sodium iodide symporter (NIS) gene.

Further, according to the present invention, there is provided a method of treating a tumor in a subject comprising the steps of:

i) administering to the subject an attenuated, tumour-targeting bacterium specific for the tumor, the bacterium comprising a heterologous nucleotide sequence encoding a protein that promotes accumulation of a radionuclide within the bacterium, and;

ii) administering to the subject a therapeutically effective amount of the radionuclide of step i. Preferably the heterologous nucleotide sequence comprises the sodium iodide symporter (NIS) gene and the radionuclide is I-131.

Also according to the present invention, there is provided a method of treating a tumor in a subject comprising, administering to the subject an attenuated, tumor targeting bacterium comprising a heterologous nucleotide sequence encoding a protein that promotes accumulation of a radionuclide within the bacterium, and wherein the bacterium comprises a therapeutically effective amount of the radionuclide. In such an embodiment the bacteria of the present invention are preloaded with radionuclide prior to administration to a subject. Preferably, the heterologous nucleotide sequence comprises the sodium iodide symporter (NIS) gene and the radionuclide is I-131.

This summary does not necessarily describe all necessary features of the invention but that the invention may also reside in a sub-combination of the described features.

DESCRIPTION OF PREFERRED EMBODIMENT

The invention relates to tumor-targeting bacteria. More specifically the present invention relates to tumor-targeting bacteria that accumulate radionuclides and the use of these bacteria to deliver a dose of radioactivity to a tumor within a subject.

The following description is of a preferred embodiment by way of example only and without limitation to the combination of features necessary for carrying the invention into effect.

According to the present invention there is provided an attenuated, tumour-targeting bacterium comprising a heterologous nucleotide sequence encoding a protein that promotes the accumulation of a radionuclide within the bacterium. The terms "bacteria of the present invention" and "tumor targeting bacteria of the present invention" are used interchangeably and refer to attenuated, tumour-targeting bacteria comprising a heterologous nucleotide sequence encoding a protein that promotes the accumulation of a radionuclide.

By the term "tumor-targeting" it is meant that the bacteria accumulate in close proximity to a tumor when the bacteria are administered to a subject. The bacteria may infiltrate a tumor, associate with the exterior of a tumor, accumulate within the vicinity of a tumor, invade tumor cells, or any combination thereof. In an embodiment of the present invention, which is not meant to be limiting in any manner, the bacteria of the present invention preferentially invade and multiply within tumors in vivo.

Any tumor targeting bacterium, or any attenuated tumor targeting bacterium may serve as a precursor for the bacteria of the present invention. Microorganisms known in the art to be tumor targeting or attenuated and tumor targeting include, but are not limited to:

Lee, (1992) and Jones et al., (1992) disclose mutants of *Salmonella typhimurium* that are able to invade human epidermoid carcinoma cells.

Pawelek et al., (1997) describe a genetically engineered, attenuated, tumor targeting *Salmonella* that exhibits little or no pathogenicity in a subject.

U.S. Pat. No. 6,080,849 discloses mutant *Salmonella* sp. that target solid tumors. The bacteria are attenuated by genetic modification of the msbB gene, providing enhanced safety and reduced pathogenicity in a subject. Specific strains that are disclosed include, but are not limited to YS8211 ATCC Accession No. 202026, YS1629 ATCC Accession No. 202025, and YS1170 ATCC accession number 202024.

U.S. Pat. No. 6,190,657 describes super-infective, tumor targeting bacteria, fungi, and protists. Further, the bacteria may be used to deliver toxic gene products such as cytosine deaminase, or cytochrome p450 oxidoreductase to tumor cells. The bacteria may also reduce tumor volume by invading and growing in tumors. Specific strains that are disclosed include, but are not limited to *Salmonella typhimurium* strain 70 (ATCC Accession No. 55686), *Salmonella typhimurium* strain 71 (ATCC Accession No. 55685), *Salmonella typhimurium* strain 72 (ATCC Accession No. 55680), *Salmonella typhimurium* strain $72^{5-3-2}$ (ATCC Accession No. 97179), *Salmonella typhimurium* strain $14028^{pop-1}$ (ATCC Accession No. 55684), *Salmonella typhimurium* strain $14028^{pop-2}$ (ATCC Accession No. 55683), *Salmonella typhimurium* strain $72^{pop-1}$ (ATCC Accession No. 55681), *Salmonella typhimurium* strain $72^{pop-2}$ (ATCC Accession No. 55682), *Salmonella typhimurium* strain YS721 (ATCC Accession No. 55788), *Salmonella typhimurium* strain YS7211 (ATCC Accession No. 55787), *Salmonella typhimurium* strain YS7212 (ATCC Accession No. 55789) and *Salmonella typhimurium* strain YS7213 (ATCC Accession No. 55786).

Specific examples of bacteria that may be used within the present invention include, but are not limited to attenuated, tumor targeting strains of *Pseudomonas radiora, Deinocuccus* sp., *Salmonella* sp., including *S. typhimurium, S. choleraesuis, S. enteritidis*, and *S. typhimurium*. A preferred strain is *S. typhimurium* R6008.

The present invention also contemplates the microorganisms listed above as progenitors of the bacteria of the present invention. The progenitor bacteria may be genetically modified to comprise a heterologous nucleotide sequence encoding a protein that promotes the accumulation of a radionuclide within the bacterium.

In another aspect of an embodiment, the present invention provides one or more microorganisms selected from the group consisting of: *Salmonella typhimurium* strain 70 (ATCC Accession No. 55686), *Salmonella typhimurium* strain 71 (ATCC Accession No. 55685), *Salmonella typhimurium* strain 72 (ATCC Accession No. 55680), *Salmonella typhimurium* strain $72^{5-3-2}$(ATCC Accession No. 97179), *Salmonella typhimurium* strain $14028^{pop-1}$ (ATCC Accession No. 55684), *Salmonella typhimurium* strain $14028^{pop}$-2 (ATCC Accession No. 55683), *Salmonella typhimurium* strain $72^{pop-1}$ (ATCC Accession No. 55681), *Salmonella typhimurium* strain $72^{pop-2}$ (ATCC Accession No. 55682), *Salmonella typhimurium* strain YS721 (ATCC Accession No. 55788), *Salmonella typhimurium* strain YS7211 (ATCC Accession No. 55787), *Salmonella typhimurium* strain YS7212 (ATCC Accession No. 55789) and *Salmonella typhimurium* strain YS7213 (ATCC Accession No. 55786), comprising a heterologous nucleotide sequence encoding a protein that promotes the accumulation of a radionuclide within the bacterium, when the bacteria is in the presence of the radionuclide Preferably, the heterologous nucleotide sequence comprises a nucleotide sequence encoding NIS. In a specific aspect of an embodiment of the present invention, which is not meant to be considered limiting in any manner, the nucleotide sequence is the human NIS sequence.

Various methods may be employed to isolate tumour-targeting bacteria, for example, but not limited to the methods described in U.S. Pat. No. 6,190,657 and WO 96/40238 (both of which are herein incorporated by reference). Thus the present invention contemplates using any tumor targeting bacteria as progenitor bacteria for the present invention.

*Deinococcus radiodurans* can tolerate radiation exposure between 5 and 15 kGy, or about 100 times more radiation than *E. coli* and approximately 1000 times more than human cells. Therefore in some applications, it may be desirable to use *D. radiodurans* for the uses as described herein. *D. radiodurans* resistance to radiation include proteins associated with RecA, pol gene products, DNA polymerase I enzymes that exact Fapy residues, 8-oxoG glycolase (Bauche, C. and Laval, J. 1999 J Bacteriol. 181(1) p 262–269). Additionally *D. radiodurans* carries multiple genomes thereby having redundant genes and multiple repair mechanisms (Battista et. al.; 1999 Trends in Microbiology 7(9) 362–363 and 2000 Curr Biol. 10(5) p 204–205). Therefore, the bacteria used as described herein may also be altered to enhance their radiation resistance properties. For example Dalrymple, GV, et. al. (1989 Radiat. Res 120(3) p 532–6) and Barrows, L R (1989 Radiat. Res 120(3) p 537–544, which are incorporated herein by reference) disclose rendering *E. coli* more radiation resistant by inserting DNA fragments or genes from *Deinoccus radiodurans* into *E. coli*.

By the term "attenuated" it is meant that the bacteria exhibit little or no toxicity when administered to a subject. Further, it is preferable that the bacteria of the present invention are not pathogenic towards normal cells and organs in a subject. The bacteria may be selected for, or modified in a manner that the risk of toxicity of the bacteria in a subject is minimal and that administration of the bacteria is well tolerated in a subject. Furthermore, it is desired that attenuation is achieved without compromising infectivity of the bacteria, for example as described in U.S. Pat. No. 6,080,849 (which is incorporated herein by reference). Preferably, the bacteria of the invention are attenuated to reduce septic shock in a subject.

The bacteria of the present invention may be attenuated by any method or combination of methods known in the art. For example, but not wishing to be limiting, bacteria may be attenuated by methods described in U.S. Pat. No. 6,190,657, WO 96/40238, U.S. Pat. No. 6,080,849 (msbB gene knockout), Roy and Coleman (1994; firA gene knockout), or in texts of vaccine development, such as, but not limited to, as described in Levine (1990; all of which are incorporated herein by reference). Methods are also known to ensure plasmid maintenance so that the modified genes are retained within the bacteria, for example but not limited to those provided by Galen et al. (1999 which is incorporated herein by reference). Further, but not to be considered limiting in any manner, the bacteria of the present invention may be attenuated by amino acid auxotrophy (Hoiseth and Stocker, 1981, which is incorporated herein by reference), genetic modification of pyrogenic lipopolysaccharides (Hone and Powell, WO97/18837, which is incorporated herein by reference), gene knock out of one or more suitable target genes, or a combination thereof using methods known within the art. Strains of attenuated tumor targeting bacteria have been shown to be well tolerated in monkeys (Lee et al., 2000) and rodents (Bermudes et al., 2000) wherein bacteria levels of $10^9$ colony forming units per gram of tumor (c.f.u./g) are observed. These studies demonstrate the safety and genetic stability of attenuated tumor targeting bacteria.

Preferably the bacteria are attenuated to reduce tumor necrosis factor septic shock, for example, but not limited as described in WO 96/40238 (which is incorporated herein by reference). Modifications to the lipid composition of tumor-targeted bacteria that alter the immune response as a result of decreased induction of TNF-α production may be, but are not limited to being performed as described in WO 96/40238 or WO97/18837 (which are incorporated herein by reference). WO97/18837 also discloses methods to produce gram negative bacteria having non-pyrogenic Lipid A or LPS in msbB, kdsA, KdsB, KdtA and htrB, etc. Further, other genetic modifications are also contemplated, for example, but not limiting to disruption of msbB(mlt) in *E. coli* (Somerville et al., 1996). Thus, the present invention contemplates bacteria that are rendered attenuated by any method. Further, the present invention contemplates strains of bacteria that are naturally attenuated.

The present invention provides a mutant *Salmonella* sp. capable of inhibiting growth of a solid tumor when administered in vivo, the *Salmonella* comprising a genetically modified msbB gene, and a heterologous nucleotide sequence encoding a protein that promotes the accumulation of a radionuclide within the bacterium, when the bacteria is in the presence of the radionuclide and wherein the mutant *Salmonella* sp. expresses an altered lipid A molecule compared to a wild-type *Salmonella* sp., and induces TNF-α expression at a level less than that induced by a wild type *Salmonella* sp. Preferably, the heterologous nucleotide sequence comprises a nucleotide sequence encoding NIS. In a specific aspect of an embodiment of the present invention, which is not meant to be considered limiting in any manner, the nucleotide sequence is the human NIS sequence.

The present invention further contemplates isolating subtypes of bacteria, or modifying the bacteria, such that the ratio of tumour targeting to normal tissue targeting bacteria is increased. By increasing this ratio, a substantial portion of the bacterial population are tumour targeting and the titre of bacteria to be administered may be reduced.

The bacteria of the present invention comprise a heterologous nucleotide sequence encoding a protein that promotes the accumulation of a radionuclide. By the term "heterologous nucleotide sequence" it is meant that the nucleotide sequence is not normally found in nature within the bacterium of the present invention. The heterologous nucleotide sequence may comprise any nucleotide sequence which is transcribed and translated into a protein that promotes the uptake and accumulation of a radionuclide in the bacteria, when the bacteria is in the vicinity of the radionuclide. For example, but not to be considered limiting in any manner, the heterologous nucleotide sequence may comprise a nucleotide sequence encoding a sodium iodide symport protein which permits the accumulation of radioiodine. The heterologous nucleotide sequence may comprise any heterologous NIS sequence known in the art for example but not limited to human NIS as disclosed in WO 97/28175, or Dia et al., (1996; which are herein incorporated by reference), or a homologue, or a derivative of human NIS that is capable of promoting the uptake and accumulation of radioiodine within the bacterium of the present invention. Examples of homologues include, but are not limited to NIS obtained from other mammals, for example rodent NIS (Dia et. al. 1996 and WO 97/28175), or other microorganisms, for example, but not limited to *Vibrio paprahaemolyticus*, *Bacillus subtilis*, and *Xanthobacter* sp. (Benvenga et. al., 1999). The term "derivative" is meant to include NIS sequences which have been genetically modified, for example, but not limited to, by site directed mutagenesis, one or more deletions, inversions, DNA duplications and the like, providing that the NIS protein retains symporter activity.

Furthermore, homologues or derivatives of NIS include nucleotide sequences that hybridize to NIS under stringent conditions as are known in the art (for example: Sambrook et al., Molecular Cloning: A Laboratory Manual, $2^{nd}$ Ed., Cold Spring Harbor Laboratory Press, 1989), or that are characterised as having at least an 80% similarity with NIS as determined using nucleotide sequence alignments programs for example but not limited to BLAST using default parameters (http://www.ncbi.nlm.nih.gov/BLAST/; using default parameters: Program: blastn; Database: nr; Expect 10; low complexity; word size 11). A homologous protein includes a protein with an amino acid sequence having at least 75%, preferably 80–90% identity with the amino acid sequence of the NIS protein. Such homology determinations may be made using oligonucleotide alignment algorithms for example, but not limited to a BLAST (GenBank URL: www.ncbi.nlm.nih.gov/cgi-bin/BLAST/, using default parameters: Program: blastp; Database: nr; Expect 10; filter: default; Alignment: pairwise; Query genetic Codes: Standard(1)) or FASTA, again using default parameters.

As will be evident to someone of skill in the art, it is preferable that the genetic construct comprising the heterologous nucleotide sequence comprises regulatory elements, and other localization sequences, which permit the heterologous nucleotide sequence comprising the NIS encoding sequence to be expressed, transported and assembled at a proper intracellular site within the bacterium of the present invention.

Any vector that permits the expression of NIS may be used as described herein. Vectors comprising a genetic construct for the production of NIS in bacteria are known in the art. For example, but not to be considered limiting in any manner, Spitzeg et al., (1998) ligated the human NIS sequence into a DNA-plasmid pBluescript-SKII(−) and developed cDNA clones using *Escherichia coli* bacteria that expressed NIS; WO 97/28175 describes commercially available plasmids for the expression of the NIS gene in procaryotes and in particular bacteria; Boland et al., (2000) developed a recombinant adenovirus strain for expression of NIS, and carried out recombinant cloning using *Escherichia coli* that expressed NIS.

The heterologous sequence of the present invention may be introduced and maintained on a plasmid, or may be integrated into the DNA of the bacterium. There are several commercially available plasmids and bacteriophage systems that are well known in the art from Invitrogen, Stratagene, Life Technologies, and Worthington, for example, but not limited to pAB2, pXL3215, p279, pEZZ18, pSP72, pBSI-IKS+ and pSP-CHT. However, as will be evident to someone of skill in the art, other plasmids or bacteriophage systems may be employed. Detailed instruction manuals for carrying out ligation, introducing the plasmid or phage to the bacteria are available from the commercial suppliers. Confirmation of the integration is made by several well known molecular biology techniques such as Southern, Northern and Western Blots (to confirm NIS DNA, RNA and protein, respectively; methods described in Sambrook et al., Molecular Cloning: A Laboratory Manual, $2^{nd}$ Ed., Cold Spring Harbor Laboratory Press, 1989, which is incorporated herein by reference). NIS protein may also be confirmed in vitro using anti-NIS antibodies in an immunoassay as is known in the art (e.g. Sambrook et al.). Any suitable plasmid may be used for this purpose, for example, but not limited to plasmids from non commercial sources or commercial sources such as Invitrogen or Stratagene.

Expression of the heterologous nucleotide sequence in the bacteria of the present invention permits the uptake and accumulation of an exogenously applied radionuclide when the bacteria are in the presence of the radionuclide. In an embodiment of the present invention wherein the attenuated, tumor targeting bacteria express a functionally active NIS protein, the bacteria are capable of taking up and accumulating exogenously applied radioiodine, radioastatine ($^{211}$At), or other radionuclide that can be transported by NIS. The NIS protein is not selective for a particular radioiodine and thus any radioiodine may be taken up by bacteria expressing NIS, for example, but not limited to $^{125}$I, $^{123}$I, $^{131}$I, etc, or a combination thereof, depending on the types of radioiodines available for transport. In such a manner, the type, concentration and dose of the radionuclide in the bacteria may be controlled.

Furthermore, other radionuclides may be used for therapeutic or diagnostic, for example imaging, purposes. Examples of these radionuclides include 99 mTc, 188-Re, and 186-Re. It is known that these radionuclides are taken up by hNIS (e.g. Dadachova E et al. 2002) and are either imported in to the cell, or they become immobilized within the NIS. Radionuclide immobilized within NIS may used for imaging, therapeutic, or both purposes, by ensuring that the radionuclide remains localized at the cell expressing hNIS.

The attenuated, tumor targeting bacteria of the present invention may be employed to treat tumors. For example, but not wishing to be limiting, the bacteria of the present invention may be employed to treat solid tumors, such as, but not limited to adenocarcinomas, astrocytomas, carcinomas, glioblastomas, lymphomas, melanomas, neuroblastomas, and sarcomas in tissues such as, but not limited to breast, colon, cervical, esophagus, liver, lung, ovarian, pancreatic, prostate, skin, stomach, testicular and uterine tissues. The bacteria of the present invention may be used to treat primary and metastatic tumors. Further, attenuated tumor targeting bacteria of the present invention that recognize and associate in close proximity to cancer cells via attachment to one or more surface antigens, may be used to treat specific tumors bearing such antigens that do not form solid masses of tumors, for example, but not limited to leukemias and similar malignancies. Also, the bacteria of the present invention may be capable of targeting multiple tumors in different tissues or cells.

The present invention also provides a method of treating a tumor in a subject. Generally, the method comprises the steps of:

i) administering to a subject an attenuated, tumor-targeting bacterium specific for the tumor being treated, the bacterium comprising a heterologous nucleotide sequence that promotes the accumulation of a radionuclide into the bacterium; and ii) administering to a subject a therapeutic amount of the radionuclide that is capable of being accumulated into the bacterium.

In a preferred embodiment the heterologous nucleotide sequence encodes NIS and the radionuclide is $^{131}$I. Preferably, the subject is a mammal, more preferably a human.

The bacteria of the present invention may be administered by any route or combination of routes known in the art. For example, but not wishing to be limiting the bacteria of the present invention may be administered orally, topically, parenterally, including but not limited to intravenously, intraperitoneally, subcutaneously, intramuscularly, intratumorally (i.e. direct injection into the tumor), or any combination thereof.

Similarly, the radionuclide may be administered to a subject by any method known in the art as discussed above for the administration of the bacteria. The radionuclide may be administered prior to, after, or at the same time as the bacteria of the present invention, or administered using bacteria preloaded with the radionuclide.

In an alternate embodiment of a method of the present invention, the bacteria of the present invention are preloaded with radionuclide before the bacteria are administered to a subject. Preloading of bacteria with radionuclide may be performed by incubating the bacteria of the present invention in a medium which contains a therapeutic dose of radionuclide so that the radionuclide is taken up by the bacteria. Thus according to the present invention there is provided a method of treating a tumor in a subject comprising the step of administering to the subject attenuated, tumor targeting bacteria that comprise a therapeutic dose of radionuclide. Preferably, the heterologous nucleotide sequence comprises a NIS sequence and the radionuclide is $^{131}$I. It is also preferred that the bacterial strains employed exhibit enhanced radiation resistance, for example, but not limited to attenuated, tumor targeting strains of *Deinococcus radiodurans*. However, such strains are not limited to being used in such embodiments.

Depending on the size and number of tumors in a subject, a dose of bacteria ranging from about 1 to about $10^8$ c.f.u./kg preferably about 1 to about $10^2$ c.f.u./kg is administered to the subject. Further, the bacteria may be allowed time to invade and grow within a tumor prior to administration of the radionuclide. Without wishing to be considered limiting in any manner, the bacteria may be administered between about 1 day and about 14 days prior to the radionuclide, to permit the bacteria of the present invention to achieve an optimal concentration in the vicinity of the tumor. Similar times are suggested by Bermudes (2000), Clairmont (2000) and U.S. Pat. No. 6,080,849. Further, prior to the administration of a therapeutic amount of $^{131}$I, or other desired radioisotope to be accumulated, a diagnostic dose ranging from 2 to 5 mCi's (74 to 185 MBq) of either $^{123}$I or $^{131}$I may be administered to a subject and a nuclear medicine imaging scan may be performed using either planar or single photon emission computed tomography (SPECT) imaging techniques to confirm in vivo the inter and intra-tumour presence of the bacteria and the functioning of the NIS gene (via confirmation of accumulation and concentration of radioiodine in bacteria), and to determine the amount of $^{131}$I required for radiotherapy. Imaging protocols and determination of radionuclide concentration are known in the art (Saha, 1998; DeNardo, 1996 and Erwin et al., 1996; all of which are incorporated herein by reference).

The present invention also contemplates administering to a subject an appropriate dose of a thyroid hormone prior to the administration of $^{131}$I to suppress thyroid stimulating hormone and thyroid uptake of $^{131}$I.

The therapeutic dose of $^{131}$I, may vary depending on tumour size, extent of metastatic sites, and NIS uptake in bacteria. A dose in an amount from about 25 to about 200 mCi's (about 925 MBq to about 7.4 GBq) may be employed in the method of the present invention. However, dosages outside the stated ranges may also be used.

Therefore, the present invention provides a method for treating a tumour is a subject comprising:

i) administering an attenuated tumour targeting bacteria to the subject;

ii) allowing the bacteria to accumulate within one or more target tumours within the subject;

iii) optionally, administering a hormone to suppress uptake of the radionuclide within non-target organs of the subject;

iv) administering a radionuclide; and v) optionally performing a diagnostic scan of the subject.

The attenuated, tumor-targeting bacteria of the present invention may also comprise nucleotide sequences encoding one or more proteins of interest that render a tumour radiation sensitive, in addition to comprising the heterologous nucleotide sequence encoding a protein that promotes the accumulation of a radionuclide. Without wishing to be limiting in any manner, the bacteria of the present invention may be genetically modified to express proteins that render tumor cells radiation sensitive, such as, but not limited to, proteins that interfere with radiation repair mechanisms, tumour cell cycle synchronization, hypoxia or any combination thereof to enhance the radio-therapeutic effect (Brown, 1989; Bentires-Alj et al., 2000; Hlavaty et al., 1999; and Lambin et. al., 2000). For example, but not wishing to be limiting, the bacteria of the present invention may be genetically modified to produce proteins that produce nitrous oxide, proteins that affect tumour promoter gene or oncogene sequence activity (eg. HER-2), suicide proteins such as, but not limited to cytosine deaminase, HSV-TK, and proteins that function as prodrug converting enzymes to enable in situ combination radiotherapy and chemotherapy, for example, but not limited to, as described in U.S. Pat. No. 6,190,657 (which is herein incorporated by reference). In such embodiments, it is preferably that the bacteria of the present invention are capable of invading tumor cells and that the protein that renders tumor cells radiation sensitive be secreted from the bacteria of the present invention. In this regard, methods of fusing signal sequences that direct secretion of proteins from bacteria to nucleotide sequences encoding specific proteins are well known in the art.

The present invention also contemplates attenuated, tumor targeting bacteria which comprise one or more nucleotide sequences that enhance radioiodine retention in bacteria. For example, but not wishing to be limiting, the bacteria of the present invention may further comprise a co-expression system including thyroperoxidase (TPO) or catalase-peroxidase. Without wishing to be bound by theory, thyroperoxidase may oxidize iodine to iodate and enhance incorporation of radioiodine onto phenolic substrates (Huang et al., 2001). Without wishing to be considered limiting in any manner, the catalase-peroxidase (KatGs) may be derived from Cyanobacterium *Synechocystis* PCC 6803 (Jakopitsch C, et al., Biochem Biophys Res Commun 2001, 287:682–7, which is herein incorporated by reference). However, other catalase-peroxidases known in the art may also be employed.

The present invention also contemplates attenuated, tumor targeting bacteria further expressing genes that improve radiation tolerance. For example, but not wishing to be limiting, Dalrymple et al., (1989) and Barrows, (1989) disclose inserting DNA fragments or genes from *D. radiodurans* into *E. coli* to enhance radiation resistance. Battista et al., (1999; 2000) describe *D. radiodurans* carrying multiple genomes thereby having redundant genes and multiple repair mechanisms. *D. radiodurans* can tolerate radiation exposure between 5 and 15 kGy, about 100 times more radiation than *E. coli* and about 1000 times more than human cells. Alternatively, but not wishing to be limiting, the attenuated, tumor targeting bacteria of the present invention may express high levels of superoxide dismutase.

The present invention further contemplates administering an antibiotic or other non-toxic reagent to a subject to control the growth or kill the attenuated, tumor-targeting bacteria of the present invention. For example, but not to be considered limiting, U.S. Pat. No. 6,190,657 discloses tumour targeting bacteria that are pre-screened to be sensitive to specific antibiotics that may be administered. U.S. Pat. No. 6,080,849 provides a means to terminate therapy by engineering attenuated tumor targeting bacteria that are susceptible to reagents such as the chelating agent ethylenediaminetetraacetic acid (EDTA). Similar attenuated, tumor targeting bacteria are fully contemplated by the present invention.

The above description is not intended to limit the claimed invention in any manner, furthermore, the discussed combination of features might not be absolutely necessary for the inventive solution.

The present invention will be further illustrated in the following examples. However, it is to be understood that these examples are for illustrative purposed only, and should not be used to limit the scope of the present invention in any manner.

EXAMPLES

Example 1

Introduction of NIS into Bacteria

The method described by Spitzweg (1998) is used to isolate NIS from human thyroid tissue, confirm by Northern blot and ligate into the DNA plasmid pBluescript-SK II (−) (Strategene). An attenuated strain of *Salmonella typhimurium* isolated for its tumor targeting properties is transfected with the NIS containing DNA plasmid following the method described by O'Callaghan and Charbit, (1990).

Confirmation of NIS expression within bacteria is performed according to Levy et al. (1997; which is herein incorporated by reference). Briefly, immunoblot analysis using SDS-9% polyacrylamide gel electrophoresis and electroblotting to nitrocellulose is performed to confirm NIS presence within transfected bacteria.

Example 2

Expression and Function of NIS

Iodide uptake in viral transfected melanoma cells is confirmed by the method of Mandell et al., (1999). Bacteria comprising NIS plasmid constructs, and control bacteria without plasmid constructs are cultured separately in multiple tubes using a suitable liquid medium to a cell density of between $10^5$ to $10^6$ or until $OD_{600\ nm}$ reaches 0.7. Iodide uptake is initiated by adding 0.5 ml of PBS containing 0.06–0.35 nM carrier-free $Na^{125}I$. Incubations are performed for a period up to 1 or 2 hours. Perchlorate inhibition of NIS is studied in tubes containing bacteria which comprise the NIS plasmid constructs wherein after 0, 15, 30, and 45 minutes following addition of $Na^{125}I$, a solution containing $NaClO_4$ in PBS is added to give a final concentration of 30 μM $NaClO_4$. Reactions are rapidly terminated by low speed centrifugation and washing the cells in ice cold PBS three times. Accumulated radioiodine is measured by placing the test tube in a standard gamma counter (Capintec or Wallac).

Alternatively, Na—I— symporter expression in *Salmonella* may be performed as follows: The human NIS gene (hNIS) or mouse NIS gene (mNIS) is subcloned into bacterial expression vectors (pTrc99A and pYA3332; high and low copy number, respectively) and then transformed into *S. typhimurium* clones (VNP20009 (41.2.9) and 8325 (41.2.9, asd-)). Selected transformants are analyzed for the presence of the NIS gene by PCR and then for NIS function by determining iodide uptake (with appropriate non-transformed controls). Bacterial transformants and controls are harvested at OD600=0.8–0.9, washed with modified Hanks balanced salt solution (HBSS) buffer containing 137 mM NaCl, 5.4 mM KCl, 1.3 mM $CaCl_2$, 0.5 mM $MgCl_2$, 0.4 mM $MgSO_4$, 0.4 mM $Na_2HPO_4$, 0.44 mM $KH_2PO_4$, 5.5 mM glucose, and 10 mM HEPES (pH 7.3), and then incubated for 1 hour at 37° C. in 0.5 ml of the same buffer containing 0.1 μCi $Na^{125}$ and 10 μM NaI to give a specific activity of 20 mCi/mmol. Duplicate samples containing 10 μM $KClO_4$ are tested for the specificity of iodide uptake. Cells are then washed with ice-cold HBSS buffer, and the cell pellets resuspended in 0.5 ml 95% ethanol. The cell-associated radioactivity of each sample is measured by liquid scintillation.

Example 3

Confirmation of Tumour Seeking and Radioiodine Accumulation and Concentration In Vivo Tumor xenografts of T47-D (breast), A549 (lung), HT-29 (colon), and LN-CAP (prostate) are prepared in SCID mice as follows: Cell lines are checked for freedom of contaminating bacteria and all operations are carried out aseptically. Cells are cultured in a suitable medium, for example a medium comprising 10% (v/v) fetal calf serum in sterile culture flasks. Cells are harvested by centrifugation and washed using sterile culture medium three times. A suspension of cells between $2\times10^5$ to $1\times10^7$ is injected into the left leg, below the knee of SCID mice. Upon visual evidence of tumor growth SCID mice are injected i.p. with a suspension of $2\times10^5$ c.f.u. of tumor-targeting bacteria comprising a NIS encoding plasmid and as controls another group of animals is injected with the same amount of tumor seeking bacteria lacking the NIS plasmid. Following a period of 2 to 5 days, animals are injected through the tail vein with 0.2 ml of a 50 Mbq amount of $^{131}$I. Image studies are conducted 12, 24, 48 and 72 h with the mice conscious in a lucite restraining device placed directly on a planar gamma camera head. Counts are obtained using standard nuclear medicine imaging procedures using a 128×128 matrix.

Example 4

Confirmation of a Therapeutic Effect In Vivo

Tumor xenografts of SCID mice are prepared as above. Tumour bearing animals include controls with no tumor seeking bacteria—one group receives an injection of NaCl and another group receives a 111 Mbq (3 MCi) dose of $^{131}$I, whereas tumour bearing animals include attenuated, tumor targeting bacteria with NIS expression and tumor seeking bacteria without NIS and both groups receive a 111 Mbq (3 MCi) dose of $^{131}$I. Nuclear medicine imaging studies is performed and all mice are followed for a period of 5 weeks.

Example 5

Increasing Iodide Uptake within Tumor Targeting Bacteria Expressing NIS

A catalase-peroxidase gene is cloned by PCR amplification from the cyanobacterium *Synechocystis* PCC 6803. Bacterial vectors pYA3332 (low copy) or pTrc99A (high copy) are employed as expression vectors in *E. coli*. The catalase-peroxidase may be, but is not limited to, the catalase-peroxidase (KatGs) from Cyanobacterium *Synechocystis* PCC 6803 (Jakopitsch C, et al., Biochem Biophys Res Commun 2001, 287:682–7, which is herein incorporated by reference). The iodide transporter and/or catalase-peroxidase is shuttled into tumor targeting *Salmonella* and radioiodide uptake is determined as indicated in Example 2.

Example 6

Polyacrylamide Gel Electrophoresis Detection of NIS Expressed in Bacteria

Bacteria harboring the NIS-containing plasmid are grown to late-log phase and harvested by centrifugation. The bacterial pellet is resuspended in phosphate buffered saline containing 0.4 mg/ml lysozyme and subjected to 3 cycles of freezing and thawing to lyse the cells. Following centrifugation to remove cell debris, the supernatant is collected, and an equal volume of 2×SDS-PAGE buffer is added. The samples are then boiled for 10 minutes and loaded onto a 10% SDS-PAGE gel, resolved by electrophoresis, and the gel stained with coomasie blue to visualize proteins.

BIBLIOGRAPHY

Adler (1973) *J. Gen. Microbiol.* 74:77–91.
Barrows, (1989) *Radiat. Res* 120(3), 537–544.
Battista et al., (1999) *Trends in Microbiology* 7(9), 362–363.
Battista et al., (2000) *Curr Biol.* 10(5), 204–205.
Bentires-Alj et al., (2000) *Cancer Gene Therapy* 7(1), 20–26
Benvenga et al., (1999) *J. Endocrinol. Invest.* 22(7), 535–540.
Bermudes et al., (2000) *Adv. Exp. Med. Biol.* 465, 57–63.
Boland et al., (2000), *Cancer Research* 60, 3484–3492.
Brown, (1989) *Int. J. Radiat. Oncol. Biol. Phys.* 16(4), 987–993.
Clairmont, C et al., (2000) *J Infect Dis* 181(6), 1996–2002.
Dadachova E., et al (2002) *Nucl. Med. Biol.* 29(1):13–18.
Dalrymple et al., (1989) *Radiat. Res* 120, (3): 532–6.
DeNardo, (1996) *J. Nuc. Med.* 37(12), 1970–1975.
Dia et al., (1996) *Nature* 379, 458–460.
Erwin et al., (1996) *Nuc Med & Biol* (23), 525–532.
Galen et al., (1999) *Infect. and Immunity* 76 (12), 6424–6433.
Habercorn, (2001) *Exp. Clin. Endocrinol.* Diabetes 109, 60–62.
Hlavaty et al., (1999) *Neoplasma* 46(5), 267–276
Huang et al., (2001) *Cancer Gene Ther August,* 612–618.
Hoiseth and Stocker., (1981) *Nature* 291, 238–239.
Jones et al., (1992) *Infect. Immun.* 60:2475–2480.
Lambin et al., (2000) *Int. J. Radiat. Biol.* 76(3), 285–293
Lee, (1992) *Proc. Natl. Acad. Sci.* 89:1847–1851.
Lee et al., (2000) *J. Infect. Dis.* 181(6) 1996–2002.
Levy et al., (1997) *Proc. Natl. Acad. Sci.* 94:5568–5573.
Mandell et al., (1999), *Cancer Research* 59, 661–668.
Mazzaferri, (1996) *Carcinoma of the follicular epithelium: radioiodine and other treatment outcomes.* Braverman, L. and Utiger, R. D. (eds) in The Thyroid: A Fundamental and Clinical Text, Lippincott-Raven p 922–945.).
O'Callaghan and Charbit (1990) *Mol Gen Genet.* 223, 156–158.
Pawelek et al., (1997) *Cancer Research* 15:4537–44.
Pawelek et al., WO 96/40238.
Roy and Coleman (1994) *J. Bacteriol* 176 (6), 1639–46.
Saha, (1998) *Fundamentals of Nuclear Pharmacy.* 4ed, 320–323.
Somerville et al., (1996) *J. Clin. Invest.* 97:359–365
Spitzeg et al., (1998) *J. Clin. Endocrinol. Metab.* 83(5) 1746–1751.
Spitzweg (1998) *J. Clin. Biol. Chem.* 83(5) 1746–1751.
Spitzweg et al. (1999) *Cancer Research* 59, 2136–2141.
Spitzweg et al., (2000) *Cancer Research* 60, 6526–6530.
Spitzweg et al., (2001) *J Clin Endo Met* 86, 3327–3331.
Spitzweg et al., (2001) *Exp. Clin. Endocrinol.* Diabetes 109, 56–50.

All publications, patents, and patent are incorporated by reference herein, as though individually incorporated by reference.

The present invention has been described with regard to preferred embodiments. However, it will be obvious to persons skilled in the art that a number of variations and modifications can be made without departing from the scope of the invention as described herein.

What is claimed is:

1. A method of treating a tumor in a subject, comprising administering to the subject an attenuated, tumour-targeting bacterium comprising a heterologous nucleotide sequence comprising a sodium iodide symporter (NIS) gene encoding a protein that promotes accumulation of a radionuclide within the bacterium.

2. A method of treating a tumor in a subject comprising the steps of:
    i) administering to the subject an attenuated, tumour-targeting bacterium specific for the tumor, the bacterium comprising a heterologous nucleotide sequence comprising a sodium iodide symporter (NIS) gene encoding a protein that promotes accumulation of a radionuclide within the bacterium, and ii) administering to the subject a therapeutically effective amount of the radionuclide.

3. The method of claim 2, wherein the radionuclide is I-131.

4. A method of treating a tumor in a subject, comprising administering to the subject an attenuated, tumor targeting bacterium comprising a heterologous nucleotide sequence comprising a sodium iodide symporter (NIS) gene encoding a protein that promotes accumulation of a radionuclide within the bacterium, wherein the bacterium comprises a therapeutically effective amount of the radionuclide.

5. The method of claim 4, wherein the radionuclide is I-131.

6. The method of claim 1, wherein the radionuclide is I-131.

* * * * *